United States Patent [19]
Hogg

[11] Patent Number: 5,746,963
[45] Date of Patent: May 5, 1998

[54] COLD FLOW CONTROL

[76] Inventor: John Moss Hogg, 122 King William, San Antonio, Tex. 78204

[21] Appl. No.: 699,043

[22] Filed: Jun. 6, 1996

Related U.S. Application Data

[63] Continuation of Ser. No. 332,366, Oct. 31, 1994, abandoned, which is a continuation-in-part of Ser. No. 134,844, Oct. 12, 1993, abandoned.

[51] Int. Cl.$^6$ .............................. B29C 45/57; A61F 2/34
[52] U.S. Cl. .......................... 264/271.1; 264/268; 623/22
[58] Field of Search ..................... 623/22, 23; 264/271.1, 264/267, 268, 259

[56] References Cited

U.S. PATENT DOCUMENTS

| | | | |
|---|---|---|---|
| 2,213,708 | 9/1940 | Lange | 428/912.2 |
| 2,616,198 | 11/1952 | Sewell | 264/320 |
| 3,470,787 | 10/1969 | Mackie | 411/377 |
| 3,609,128 | 9/1971 | Johns | 528/362 |
| 3,980,570 | 9/1976 | Okuda et al. | 252/12.4 |
| 4,007,071 | 2/1977 | Addie et at. | 156/148 |
| 4,105,816 | 8/1978 | Hori | 428/159 |
| 4,280,535 | 7/1981 | Willis | 138/112 |
| 4,380,564 | 4/1983 | Cancio et al. | 428/167 |
| 4,409,277 | 10/1983 | Michel | 428/156 |
| 4,502,161 | 3/1985 | Wall | 623/22 |
| 4,563,778 | 1/1986 | Roche et al. | 623/22 |
| 4,566,138 | 1/1986 | Lewis et al. | 623/22 |
| 4,724,110 | 2/1988 | Arnold | 264/102 |
| 4,819,582 | 4/1989 | Lichvar | 119/474 |
| 5,171,286 | 12/1992 | Lawes et al. | 623/22 |
| 5,609,638 | 3/1997 | Price et al. | 623/20 |

*Primary Examiner*—Catherine Timm

[57] ABSTRACT

This is basically an Engineering design of a means to control the stability and or resistivity of certain materials subject to Cold Flow without materially decreasing the material's normal function. This does not require additional thickness and/or hardening which may increase the resistance of the material. This method overcomes these limitations. This is accomplished by my development of a system of encapsulation, adding certain types of fibers, or both as may be required. The subject material using this method can then be processed to meet specific pressures and resistivity. There are many uses for this method, for example this method can be used for constructing the cartilage for an artificial joint where it is desired to have a predetermined force for separation and yet have low resistivity to normal motion. Another example is to apply this method to plastic bearings and bushings in order to reduce cold flow with little or no change in resistivity.

2 Claims, 1 Drawing Sheet

5,746,963

COLD FLOW CONTROL

This application is a continuation of application Ser. No. 08/332,366, filed Oct. 31, 1994, now abandoned which is a continuation-in-part of Ser. No. 08/134,844 filed Oct. 12, 1993, now abandoned.

BACKGROUND OF THE INVENTION

1. Technical Field

This invention is directed to Engineering of methods to control resistance to change in shape of, and/or resist another object to pass through, a viscous material that is subject to the property of Cold Flow.

2. Description of the Prior Art

Current attempts to control cold flow of a viscous material depend on thickness, hardness, firmness of a combination of these.

SUMMARY OF THE INVENTION

A characteristic of viscous materials when constant pressure is applied by another object that allows that object to pass through the viscous material is called cold flow. This invention furnishes a method to control cold flow of the viscous material through encapsulation of the viscous material insertion of certain fibers into the subject viscous material, or both.

BRIEF DESCRIPTION OF THE DRAWINGS

Drawing in FIG. 1 is a cutaway drawing of a possible use of this method of controlling cold flow which shows an artificial prosthesis joint where the artificial cartilage is constructed so as to control Cold Flow to specific parameters by use of encapsulation, adding certain fibers, or both.

DESCRIPTION OF THE PREFERRED EMBODIMENTS

Some solid materials have a property that allows other solid materials to pass through them; this is known as Cold Flow. These materials are viscous materials. What happens when these materials are used is shown in the following examples;

a weighted string will pass through a block of ice without separating the block into parts. It could also apply to the slow displacement of one material by another material under pressure, i.e. a block of viscous plastic resisting the movement of a metal ball which is under pressure which gradually passes its way through the viscous plastic as the viscous plastic slowly flows out of the ball's way and around it. Cold flow can be controlled, stopped or slowed down by encapsulation of the viscous material being passed through, by adding fibers or both. The encapsulating material must be nonviscous or have a higher resistance to viscous flow than the viscous material which forms the host body so that expansion and change in shape of the viscous material is restricted. The encapsulating material and the fibers must also be compatible with the viscous material of the host body. Determination must be made as to whether the fibers added are to be brittle or malleable; the amount, length, pattern of placement, and size, of the fibers added will determine how much Cold Flow will be affected and the basic function of the material that is being controlled will be affected.

Figure 1:
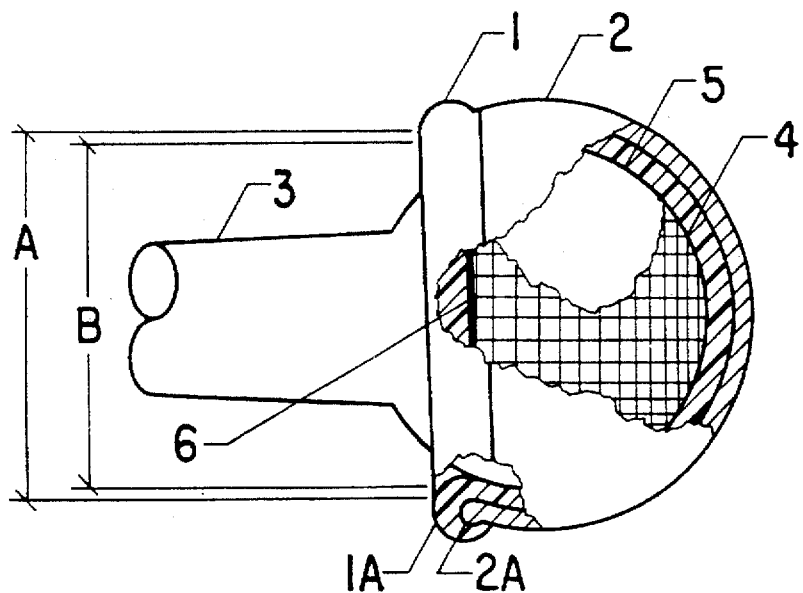

Drawing FIG. 1 is an example of how this invention can be used in an artificial prosthesis by controlling the cold flow in the artificial cartilage. In this drawing the dimension "A" is the diameter of the opening of the outside shell "2". "B" is the diameter of the ball "5" which is less than "A". This difference is filled by an encapsulated viscous artificial cartilage "1". The inside of the viscous artificial cartilage, where the ball is in contact and supported by it, is not encapsulated. This area may require a web mesh "4" as part of the encapsulation to maintain shape of and distribute stress to the viscous material with minimum change of it's function.

"1" can have fibers added to increase it's resistance to cold flow. "1A" is a cutaway of the artificial cartilage showing the artificial cartilage wraparound of the rounded end "2A" of the opening of the shell "2". "6" shows the ring joint formed where the unencapsulated surface joins the encapsulated part of the artificial cartilage. "3" represents the shaft or means to be used to connect the ball "5" to it's functional part.

Figure 2:
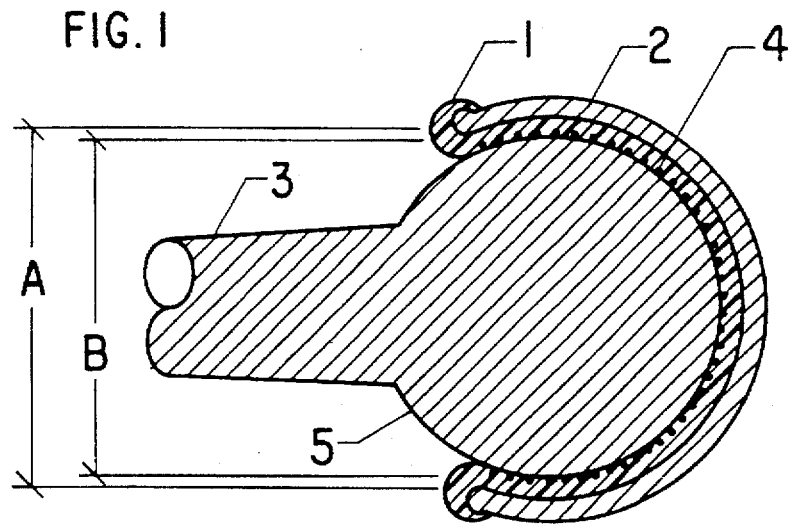
FIG. 2 is a cross section down the middle of FIG. 1 furnished to assist understanding of FIG. 1.

Drawing FIG. 2 is showing a cutaway down the middle of the Drawing FIG. 1. All letters and numbers are the same as explained for FIG. 1. The dots "4" spaced around the ball indicate, the cut through the webbing. The pressure required to cause separation of the ball from the socket in the sample illustration shown and described as FIG. 1 can be predetermined by the difference between "A" and "B", whether encapsulated or not (how and by what), type, size, amount and pattern of the fibers used to control Cold Flow.

Figure 3:
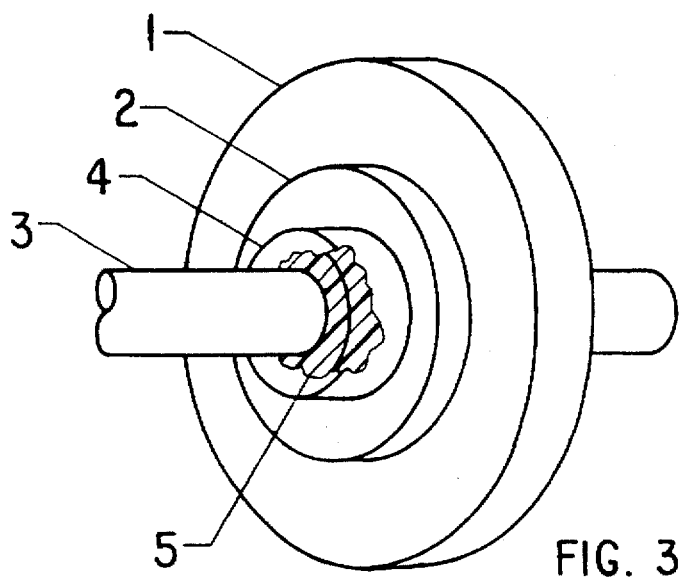
FIG. 3 is a cutaway drawing of a plastic bearing in the hub of a wheel where cold form can be controlled by adding fibers and encapsulation.

Drawing FIG. 3 is another example of a possible use of my invention as it can be used in a plastic bearing for a wheel. "1" is the wheel, "2" is the hub, "3" is the axle, "4" is the encapsulation and "5" is the viscous plastic bearing for the wheel that would have fibers added as needed to control Cold Flow.

While these are numerous materials that can be used, especially in cold flow control, the following materials currently in use for prosthesis would also be suitable; 1). cobalt—chrominum—molybdenum (Co—Cr—Mo) alloy or 2). titanium—aluminum—vanadium (Ti—6Al—4V) alloy—both could use an acetabular bearing service composed of an ultra-high molecular weight polyethylene between shell and femoral unit.

To assist growth to the metal, where desired, a porous coating of beads made of the same substance alloys. Fibers of pure titanium or Ti—6Al—4V can be used for this purpose and also to vary the restivity to cold flow in the viscous material.

What is claimed is:

1. A method of controlling the cold flow of artificial cartilage located within a ball and socket joint of a prosthesis comprising the steps of:

providing a solid viscous material;

providing a shell formed of a compatible nonviscous material or a material with a viscosity which is higher than the viscosity of the viscous material;

encapsulating the viscous material between the shell and a web mesh lining, thus restricting expansion, change in shape, cold flow of the viscous material and force required to separate ball from socket, the viscous material forming the artificial cartilage within the socket; and fitting the ball within the socket so the ball is adjacent to the web mesh to form the ball and socket joint of the prosthesis, wherein the web mesh maintains the shape of and distributes stress to the artificial cartilage during use and further controls cold flow.

2. The method of controlling cold flow as recited in claim 1, wherein fibers are added to the viscous material in a predetermined amount to further control cold flow, the amount depending on the level of resistance of the artificial cartilage to cold flow desired.

* * * * *